United States Patent [19]
Braig et al.

[11] Patent Number: 5,282,473
[45] Date of Patent: Feb. 1, 1994

[54] SIDESTREAM INFRARED GAS ANALYZER REQUIRING SMALL SAMPLE VOLUMES

[75] Inventors: James R. Braig, Oakland, Calif.; Daniel S. Goldberger, Boulder, Colo.

[73] Assignee: Critikon, Inc., Tampa, Fla.

[21] Appl. No.: 976,145

[22] Filed: Nov. 10, 1992

[51] Int. Cl.⁵ .............................. A61B 5/097
[52] U.S. Cl. ....................... 128/664; 128/719
[58] Field of Search ............ 128/716, 719, 725, 730, 128/633, 664–665, 207.14–207.17, 204.22, 205.12, 200.26

[56] References Cited

U.S. PATENT DOCUMENTS

| | | | |
|---|---|---|---|
| 3,725,658 | 4/1973 | Stanley et al. | 128/719 X |
| 4,177,381 | 12/1979 | McClatchie et al. | 250/343 |
| 4,297,871 | 11/1981 | Wright et al. | 128/719 X |
| 4,558,708 | 12/1985 | Labuda et al. | 128/719 |
| 4,692,621 | 9/1987 | Passaro et al. | 250/343 |
| 4,852,583 | 8/1989 | Walker | 128/719 X |
| 5,067,492 | 11/1991 | Yelderman et al. | 128/719 |
| 5,081,998 | 1/1992 | Yelderman et al. | 128/719 |
| 5,095,913 | 3/1992 | Yelderman et al. | 128/719 |

Primary Examiner—Angela D. Sykes
Attorney, Agent, or Firm—Woodcock Washburn Kurtz Mackiewicz & Norris

[57] ABSTRACT

An infrared gas analyzer implementing an optically stabilized detector in a sidestream configuration. In order to reduce the pneumatic sampling volume, an "optical funnel" or collimator is used to resize the optical aperture of a multi-channel optically stabilized detector without compromising signal strength. The smaller pneumatic volume is desirable in order to minimize the time required for a gas wavefront from the sample cell to traverse the optical aperture, thereby minimizing pneumatic response time. The geometry of the sample cell of the invention is also streamlined so that sharp corners or transitions which might induce turbulent gas flow are eliminated. The sample cell of the invention thus promotes smooth, laminar flow of aspirated respiratory gases through the optical aperture so as to preserve the temporal relationship of gas concentration wavefronts within the gas stream and to thereby allow the analyzer to exhibit a faster pneumatic response.

7 Claims, 4 Drawing Sheets

SIDESTREAM INFRARED GAS ANALYZER REQUIRING SMALL SAMPLE VOLUMES

BACKGROUND OF THE INVENTION

1. Field of the Invention

The present invention relates to a sidestream infrared gas analyzer for continuously determining the concentration of the constituents of the respiratory gases of a patient. In particular, the present invention relates to a sidestream infrared gas analyzer employing an "optical funnel" to resize the optical aperture of a multi-channel detector without compromising signal strength, thereby allowing a smaller sample volume to be used for measurement.

2. Description of the Prior Art

It is frequently of critical importance to monitor the concentration of carbon dioxide ($CO_2$) in the gases inspired and expired from a patient under anesthesia, for expired $CO_2$ concentration is a reliable indicator of the carbon dioxide concentration in the arterial blood. In a clinical setting, monitoring expired $CO_2$ prevents malfunctions in anesthesia rebreathing apparatus from going undetected and delivering excessive amounts of $CO_2$ to the patient. Rebreathing of anesthetic gases is very cost effective and environmentally desirable, but accurate $CO_2$ concentrations are difficult to maintain in the patient's circuit without a concentration monitor.

It is known that by directing infrared radiation through a sample of a gaseous mixture and measuring the incident radiation illuminating a detecting device, a measure of the infrared absorption of the gas can be obtained. Electrical signals produced by such a detecting device are indicative of the infrared absorption of the gas and can be processed to produce an output indicating the concentration of one or more of the constituents of the gas being analyzed. This type of gas analyzer operates on the principle that various gases exhibit substantially increased absorption characteristics at specific wavelengths in the infrared spectrum and that higher gas concentrations exhibit proportionally greater absorption.

Infrared respiratory gas analyzers for use in critical care applications come in two pneumatic configurations, namely, mainstream and sidestream. A mainstream analyzer is placed in the patient's respiratory circuit and measures the absorption of infrared light transmitted through the patient's inspired and expired respiratory gases as they flow through the respiratory circuit. Such a mainstream infrared gas analyzer is described in detail by Yelderman et al. in U.S. Pat. Nos. 5,081,998 and 5,095,913 assigned to the present Assignee and hereby incorporated by reference in their entirety. These applications describe an infrared detector and a shutterless optically stabilized capnograph which has no moving parts, which does not require a modulated source of infrared radiation, and which does not suffer from thermal drift. The disclosed infrared detector includes a substantially identical pair of thermopile detectors mounted on the same ceramic substrate and connected in series opposition. Because of this configuration, balanced and equal incident radiation illuminating the pair will produce no signal. Also, because the reference junctions of both detectors are on the same ceramic substrate and at substantially the same temperature, a drift in substrate temperature will produce no discernible change in output signal. In order to make the system respond to incident radiation, an optical filter, or attenuator, with a transmission coefficient of approximately 0.50 is placed over one of the thermopile detectors in the pair. With the filter in place, the system responds to incident radiation but is substantially insensitive to other thermal changes since the effect of a variation in background signals is compensated by subtracting the outputs of the two thermopile detectors. It is desirable to construct a sidestream infrared gas analyzer configuration which implements such infrared detectors. The present invention has been designed for this purpose.

Conventional sidestream analyzers draw a small, continuous sample of the respiratory gases through a fixed sample cell and out through an exhaust port of the sample cell. The analyzer then measures the absorption of infrared light as it is transmitted through the sample cell. Typically, a sidestream analyzer requires a pneumatic sample system which incorporates pumps, tubing and fittings. The sample system may also require valves, flow controls, pressure controls and moisture filters or separation devices. For example, a simple configuration which uses a pump to supply the sample gas to the sample cell is illustrated by Passaro et al. in U.S. Pat. No. 4,692,621. Conventional mainstream infrared gas analyzer configurations, on the other hand, take advantage of the primary flow of the respiratory gases and hence do not require the additional complexity of a pneumatic system such as those used in prior art sidestream infrared gas analyzer configurations. It is thus desired in accordance with the present invention to minimize the complexity of the pneumatic system of the sidestream gas analyzer while also improving efficiency.

A mainstream infrared gas analyzer of the type described in the aforementioned Yelderman et al. patents requires the optical and electronic components to be physically connected to the patient's airway or respiratory circuit. As a result, a mainstream gas analyzer may be subjected to mechanical abuse and temperature variations when in use. A sidestream configuration, on the other hand, allows the optical components to be remotely located from the patient's respiratory circuit so that the optical and electronic components (i.e., the optical bench) can be protected by a fixed, temperature controlled housing. Thus, while a mainstream configuration has the advantage of reduced complexity, sidestream configurations are often desired since they have the advantage of protection from damage and thermal gradients.

Conventional sidestream optical benches use infrared detectors which must be stabilized by mechanical chopping techniques. As just noted, conventional sidestream optical benches also require accurate temperature control of the detector environment to assure stability. For example, such a conventional sidestream infrared gas analyzer is disclosed by McClatchie et al. in U.S. Pat. No. 4,177,381. McClatchie et al. therein describe an infrared gas analyzer which utilizes mechanical choppers and temperature controllers in their measurements. McClatchie et al. also utilize a sample cell which directs the air therein so as to prevent direct impingement of oils, particulate matter and other contaminants onto the infrared transparent windows so as to prevent contamination of the windows. Unfortunately, this system is quite complex and expensive and relatively unreliable because of the numerous mechanical elements. A simpler, more reliable sidestream gas analyzer is desired.

Accordingly, an infrared gas analyzer in a sidestream configuration is desired which includes an optically stabilized detector having no moving parts, requiring no temperature control, consuming little power and having a reduced cost, thereby overcoming the problems of conventional sidestream configurations. The present invention has been designed to meet these needs.

SUMMARY OF THE INVENTION

The present invention uses an optically stabilized infrared detector of the type described in the aforementioned Yelderman et al. patents and a temperature controlled, high output source of the type described by way of example in related U.S. patent application Ser. No. 07/782,990, filed Oct. 28, 1991, and assigned to the present Assignee to build a simple optical bench suitable for use in a sidestream respiratory gas analyzer. Since the source and detector in these patents and patent application were originally developed for use in a mainstream configuration so as to tolerate thermal instability, there is no additional temperature control or conditioning required when these elements are placed in a sidestream configuration. As will be apparent to one skilled in the art, such a configuration in accordance with the present invention reduces system complexity, cost and power consumption. Another advantage of the present invention is that an optically stabilized infrared detector requires no mechanical chopper or shutter to maintain detector stability, thereby further reducing system complexity, cost and power consumption. In addition, since the resulting optical bench has no moving parts, routine maintenance of motors, bearings or pivots is eliminated so that reliability is thereby improved.

The present invention is further characterized by the use of an "optical funnel" or collimator for resizing the optical aperture of a multi-channel detector of the type described in the aforementioned Yelderman et al. patents without compromising signal strength. The smaller effective aperture permits a smaller pneumatic volume to be used in the sample cell, which is desirable in order to minimize the time required for wavefronts to traverse the aperture and hence to minimize the pneumatic response time. For example, in a preferred embodiment of the invention, an eight channel detector having a rectangular aperture with dimensions 0.220"×0.300" is disposed adjacent an optical funnel in accordance with the invention so as to reduce the effective aperture to 0.100" by 0.300".

In accordance with another aspect of the invention, the geometry of the sample cell is streamlined so that sharp corners or transitions which might induce turbulent gas flow are eliminated. The design of the sample cell of the invention promotes smooth, laminar flow of aspirated respiratory gases through the optical aperture, which preserves the temporal relationship of gas concentration wavefronts within the gas stream and allows the analyzer of the invention to exhibit faster pneumatic response. For example, in a preferred embodiment of the invention, the gas passage within the sample cell makes a smooth transition from a 0.060" diameter cross-section to a 0.100" diameter cross-section and then makes a smooth transition to a 0.100" by 0.100" square cross-section at the portion of the sample cell which is in the optical path of the infrared source and detector. The present invention thus functions to reduce not only the optical aperture but also to smoothly transition the gas passage so as to provide a faster pneumatic response in a compact sidestream configuration.

A preferred embodiment of a sidestream infrared gas analyzer in accordance with the invention detects the concentration of a gaseous component of a substantially gaseous flow stream provided via an airway off of the patient's main airway. In accordance with the invention, such a gas analyzer preferably comprises a source of infrared radiation having a first aperture and an infrared energy detector disposed in an optical path of the infrared radiation so as to receive incident radiation from the infrared radiation source and to produce electrical signals representative of the received incident radiation. The infrared energy detector has a second aperture which may or may not be the same size as the first aperture.

The gas analyzer of the invention is characterized by a sample cell disposed in a plane substantially perpendicular to the optical path for directing at least a portion of the substantially gaseous flow stream between the infrared radiation source and the detector via a detection volume in the optical path. Preferably, the sample cell comprises an air passage for the substantially gaseous flow stream which has a cross-section which smoothly changes from a cross-section of the airway to a first aperture of the detection volume in a plane substantially parallel to the optical path so as to prevent turbulence in the substantially gaseous flow stream as it passes through the air passage and the detection volume.

The gas analyzer of the invention is further characterized by first and second optical funnels in the housing of the infrared source and detectors. The first optical funnel is disposed in the optical path between the infrared radiation source and the detection volume for reducing a cross-section of the first aperture to a second aperture of the detection volume in a plane substantially perpendicular to the optical path without a measurable reduction in signal strength of the infrared radiation from the infrared radiation source as it passes through the first optical funnel and the detection volume. The second optical funnel, on the other hand, is disposed in the optical path between the detection volume and the infrared energy detector for increasing a cross-section of the second aperture of the detection volume to a cross-section of the second aperture without a measurable reduction in signal strength of the infrared radiation from the infrared radiation source as it passes through the second optical funnel and the second aperture for detection by the infrared radiation detector.

Processing means are also provided in accordance with the invention for processing the electrical signals representative of the received incident radiation so as to produce an indication of the concentration of the gaseous component in the substantially gaseous flow stream. In addition, the infrared radiation source and the infrared energy detector are preferably housed opposite each other in their housing so that their optical axes are aligned. Preferably, the sample cell is removable from the housing for cleaning and the sample cell further includes optical windows on either side thereof in the optical path which are calibrated to account for differential absorption effects, thereby allowing the sample cell to be interchangeable. The first and second optical funnels are also preferably treated by a material such as gold over a nickel plating so that they are highly reflective of the infrared radiation.

BRIEF DESCRIPTION OF THE DRAWINGS

The above and other objects and advantages of the invention will become more apparent and more readily appreciated from the following detailed description of the presently preferred exemplary embodiments of the invention taken in conjunction with the accompanying drawings, of which.

DETAILED DESCRIPTION OF THE PREFERRED EMBODIMENT

The above-mentioned objects and advantages of the invention will now be described with reference to FIGS. 1-4. Those skilled in the art will appreciate that the description given with respect to those figures is for purposes of description only and is not intended in any way to limit the scope of the invention. The proper scope of the invention may be determined by referring to the appended claims.

Figure 1:
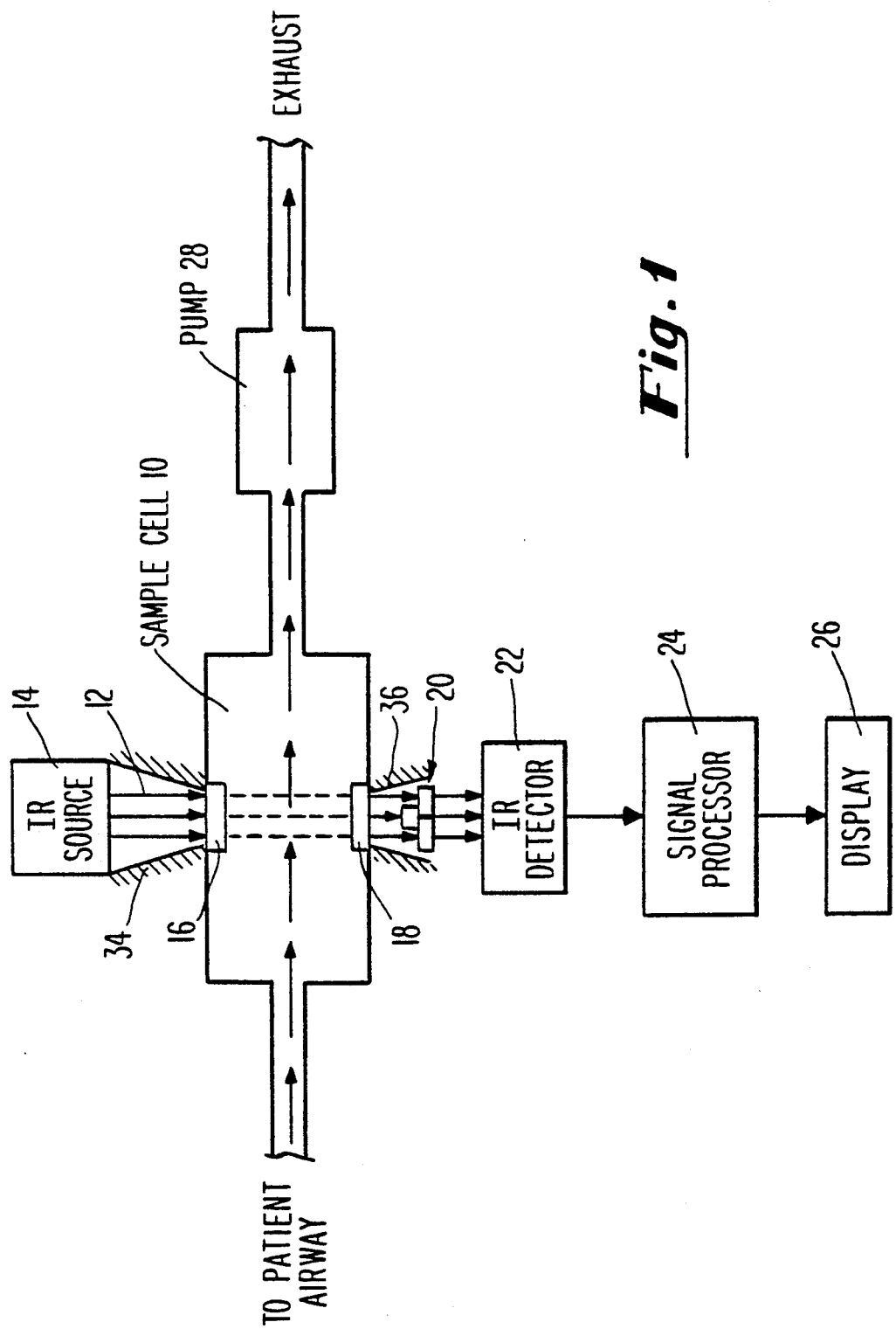
FIG. 1 illustrates a simplified block diagram of a sidestream infrared gas analyzer in accordance with the invention.

FIG. 1 illustrates a simplified block diagram of a preferred embodiment of a sidestream infrared gas analyzer in accordance with the invention. As shown, a sample gas stream taken from the patient's main respiratory airway is directed into a sample cell 10. At sample cell 10, infrared light 12 from an infrared source 14, which is preferably of the type described in the aforementioned commonly owned patent application Ser. No. 07/782,990, now U.S. Pat. No. 5,247,185 passes through window 16 into sample cell 10 and through the gas to be analyzed. The infrared light 12 passing through the gas in the sample cell 10 is then selectively absorbed by the constituents in the gas stream, and the attenuated infrared light 12 exits sample cell 10 via window 18. The attenuated infrared light 12 then passes through filters 20 to selectively filter the infrared light at the respective frequencies of the different constituents. The filtered infrared light 12 then impinges upon infrared detector 22, which is preferably an infrared detector of the type described in the aforementioned Yelderman et al. patents. As described in those patents, infrared detector 22 converts the received light into electrical signals which can be processed by signal processor 24 into values indicative of the concentration of the respective constituents in the gas flow stream. This information is then presented to the user via display 26. As also shown in FIG. 1, pneumatic components such as pump 28 are generally provided for supplying the sample gas from the patients's airway to the sample cell 10 via an inlet tube. However, since the pneumatic volume required for measurement in accordance with the invention is substantially reduced, the power consumption and complexity of the pneumatic components may be correspondingly reduced.

Figure 2:
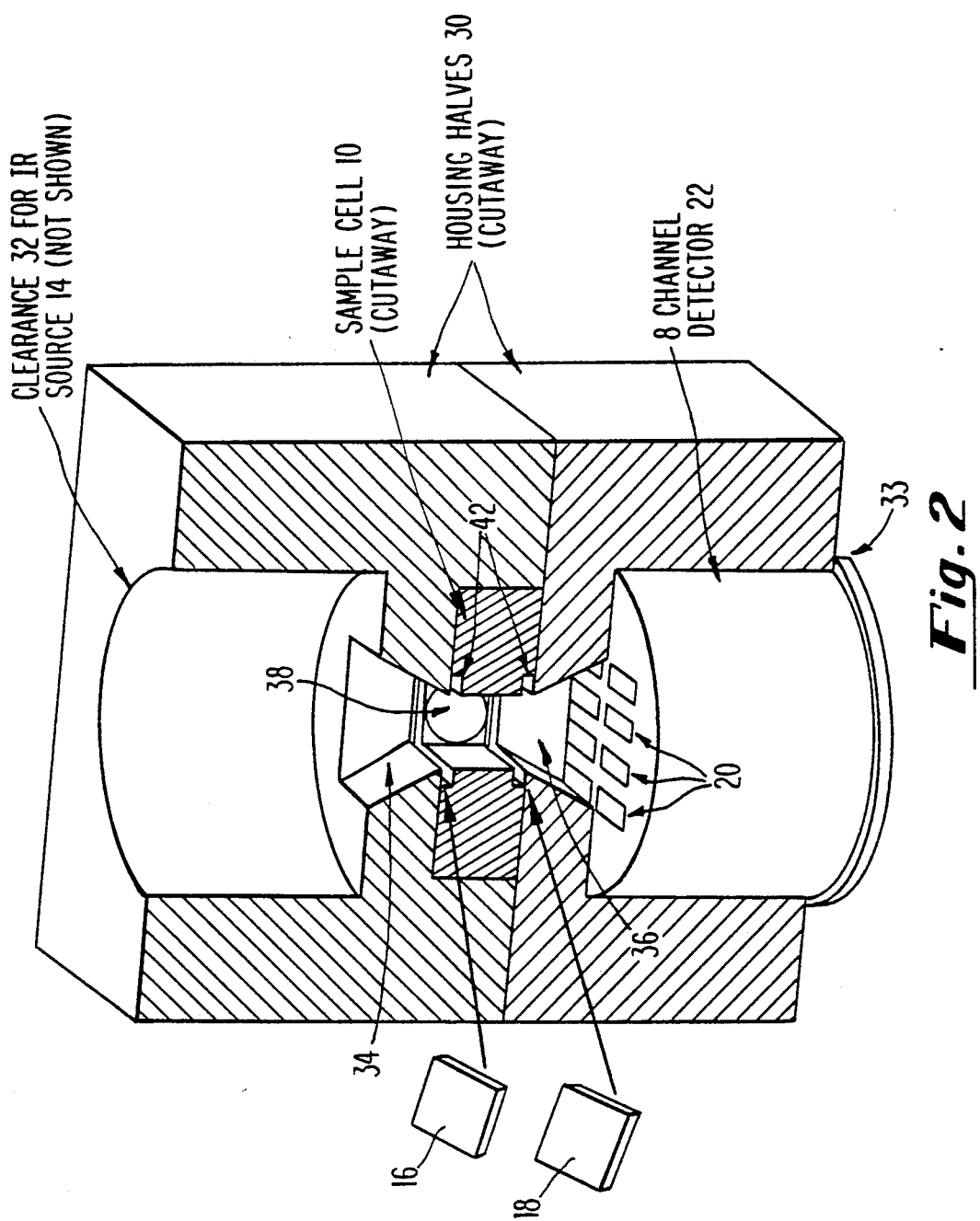
FIG. 2 illustrates a cutaway view of a sidestream infrared gas analyzer in accordance with the invention.

As shown in FIG. 2, the infrared source 14 and the infrared detector 22 of the invention are preferably mounted in opposite housing halves 30 so that their optical axes are aligned. As shown, housing halves 30 include clearance 32 for accommodating the infrared source 14 and a separate cavity 33 for accommodating infrared detector 22. In a preferred embodiment, infrared detector 22 comprises eight constituent channels including one reference channel but may include a different number of constituent channels as would be apparent to those skilled in the art.

In a preferred embodiment, the infrared source 14 and the infrared detector 22 have rectangular optical apertures of approximately 0.220" by 0.300"; however, these apertures need not be the same size and shape. As noted above, it is desired in accordance with the invention to minimize the pneumatic volume which intersects the optical path so that pneumatic response time may be improved. This requires that the optical aperture be correspondingly reduced. For this purpose, "optical funnels" 34 and 36 are created in the respective housing halves 30 to reduce the rectangular optical apertures of the infrared source 14 and the infrared detector 22. In a preferred embodiment, the rectangular optical apertures of the infrared source 14 and infrared detector 22 are reduced to approximately 0.100" by 0.300", thereby reducing by approximately 50% the respective aperture areas at the windows 16 and 18. Preferably, the walls of the optical funnels or "collimators" are treated by plating or painting a thin layer of gold over a nickel plating so that the optical funnels are highly reflective at the infrared wavelengths output by the infrared source 14. As will be appreciated by those skilled in the art, optical funnels 34 and 36 collect light efficiently but need not maintain a one to one correspondence between the infrared light emitted by infrared source 14 and the light detected by infrared detector 22 since the present invention does not perform any imaging functions. As will also be appreciated by those skilled in the art, reflective optical funnels 34 and 36 allow the sidestream infrared gas analyzer of the invention to resize the optical apertures of the infrared source 14 and the infrared detector 22 to permit a smaller pneumatic volume without compromising signal strength.

Figure 3:
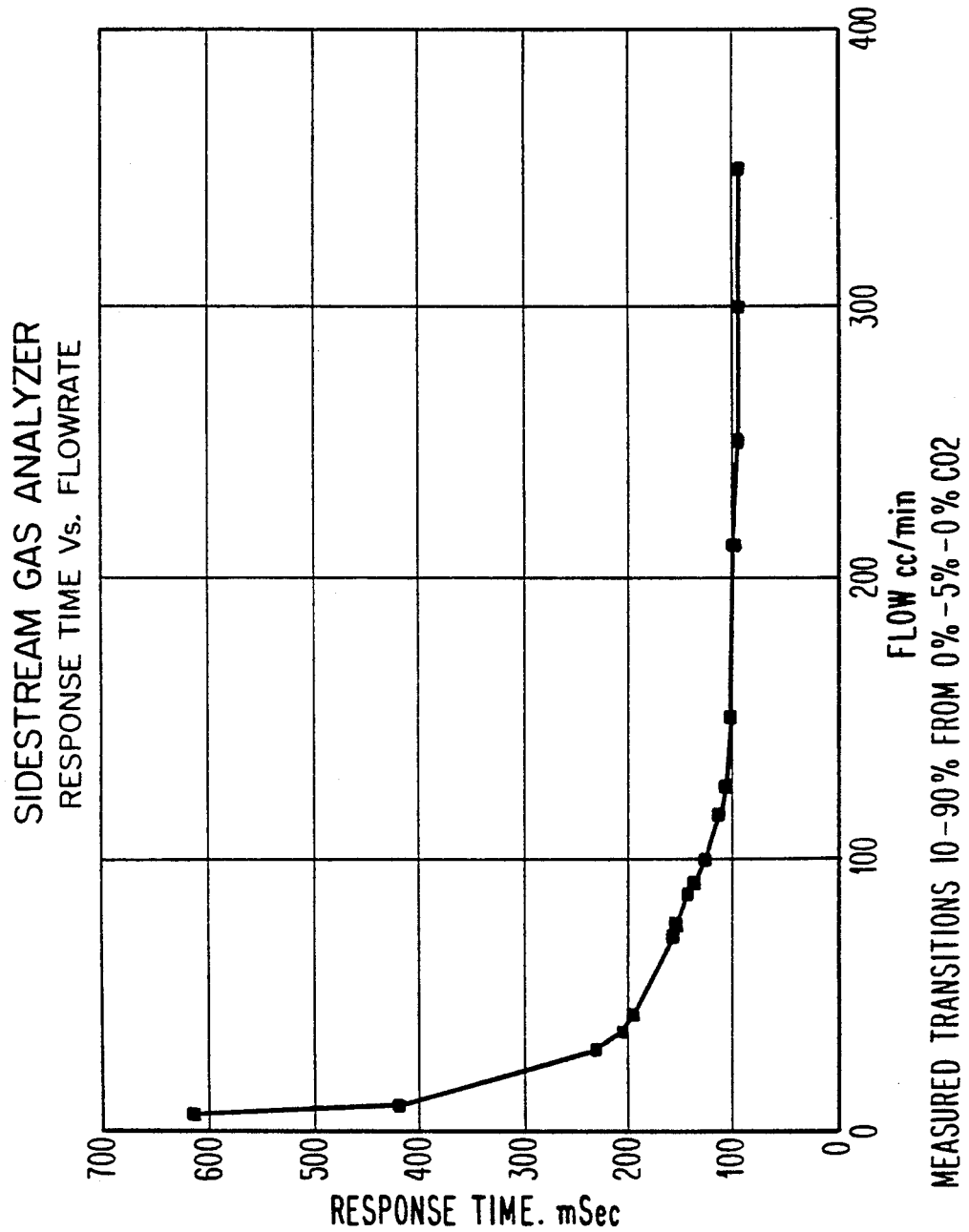
FIG. 3 illustrates the effect that the pneumatic flow rate has on response time.

FIG. 3 illustrates the effect that pneumatic flow rate has on response time of a sidestream infrared gas analyzer of the type described herein. As shown in FIG. 3, response time can be significantly reduced to approximately 100 msec for pneumatic flow rates on the order of 125 cc/minute. Accordingly, the sample cell 10 of the present invention has also been redesigned to minimize the cross-section of the gas passageway so as to improve pneumatic flow rate without using additional pumps, tubing, fittings, valves, flow controls, pressure controls and the like as in prior art sidestream infrared gas analyzers. The redesigned sample cell 10 in accordance with the invention is preferably removable from housing halves 30 for cleaning and is interchangeable with other such sample cells. In order to ensure interchangeability, the sample cell 10 is calibrated to account for differential absorption effects amongst the sample cell windows 16 and 18 using techniques such as those described by Yelderman et al. in U.S. Pat. No. 5,067,492, assigned to the same assignee as the present invention and the contents of which are hereby incorporated by reference. Preferably, sample cell 10 is also made of inexpensive metal or plastic so that it is readily disposable. The primary function of sample cell 10 is to provide a channel for the flow of respiratory gases which is substantially perpendicular to the optical aperture at windows 16 and 18 and hence substantially perpendicular to the optical path between infrared source 14 and infrared detector 22. As will be described below, such a perpendicular configuration allows the optical path length to be substantially reduced and the pneumatic sample volume to be reduced so that the measured gas volume can pass through the detection volume very quickly.

Figure 4:
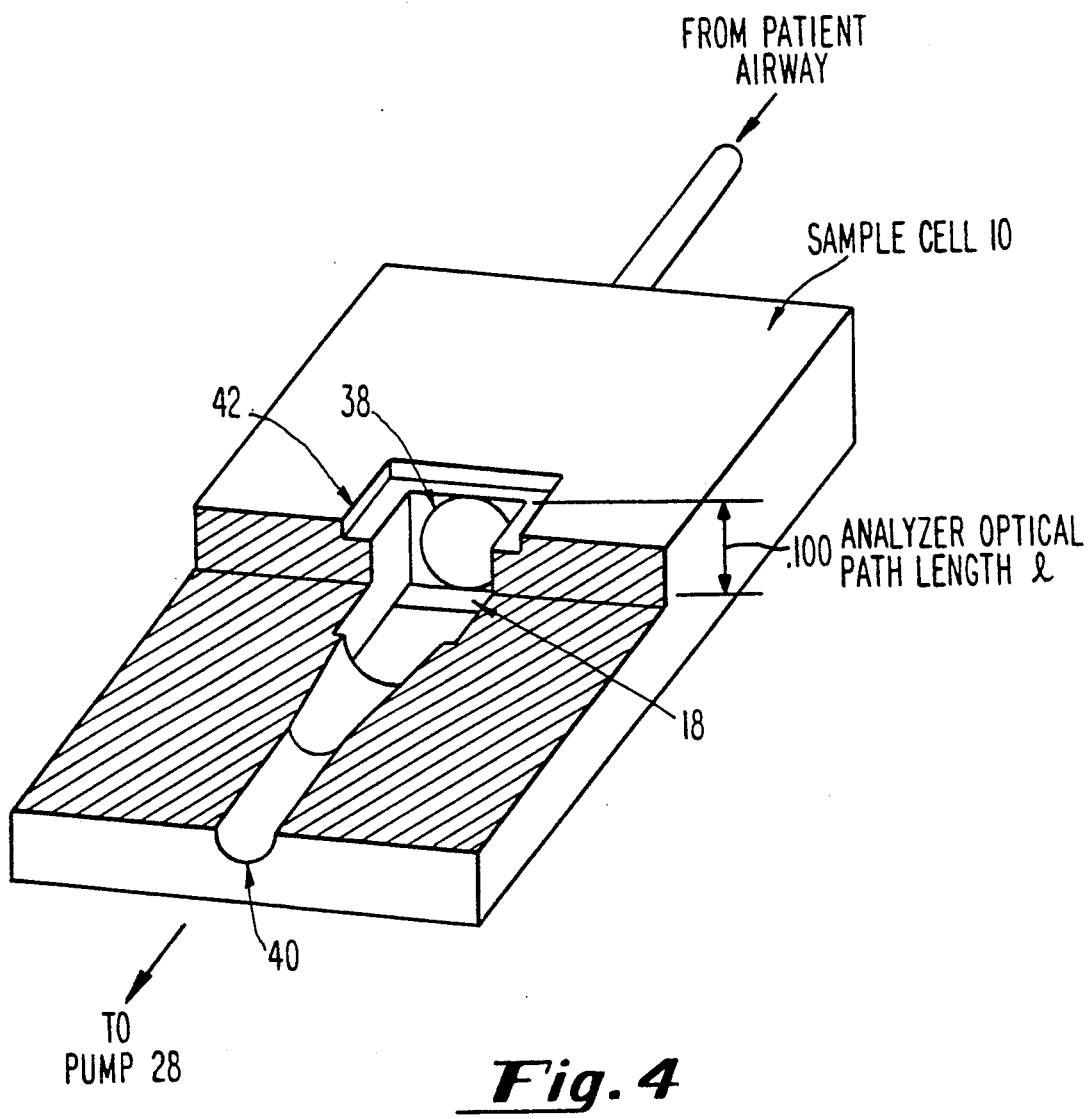
FIG. 4 illustrates a cutaway view of a sample cell for a sidestream infrared gas analyzer in accordance with a preferred embodiment of the invention.

As illustrated in FIG. 4, gas from the patient airway is connected to an input on the back side of sample cell 10 and then passes through a gas passageway 40 which is shaped so as to create smooth transitions from the round cross section at the gas tube inlet connection. Similarly, gas which has passed through an optical detection volume passes through the other end of gas passageway 40 and then to the gas tube outlet connected to pump 28. Gas passageway 40 is thus substantially symmetrical on either side of the optical path and smoothly transitions from the round cross-section at the gas inlet and outlet to the rectangular cross-section at the aperture 38 where the gas passageway intersects the optical path to define the detection volume within the sample cell 10. This detection volume is defined on two opposing sides by the walls of the sample cell 10, on two opposing sides by apertures 38 of gas passageway 40, and on two opposing sides by windows 16 and 18, which are preferably disposed on ledges 42 and sealed so as to enclose the detection volume. Preferably, optical windows 16 and 18 are formed of anti-reflective coated silicon or sapphire and arranged on opposite sides of sample cell 10 as illustrated in FIG. 4 so that windows 16 and 18 align with the optical axis (optical path) of the infrared source 14 and infrared detector 22.

The sensitivity and signal to noise ratio of the sidestream infrared gas analyzer in accordance with the invention are determined by the optical path length, 1, which, as shown in FIG. 4, is the distance in the detection volume between windows 16 and 18. A short path length gives low sensitivity but high signal to noise ratio. On the other hand, a long path length provides high sensitivity but low signal to noise ratio. In a preferred embodiment of the invention, the path length is 0.100" so as to provide an optimum tradeoff between sensitivity and signal to noise ratio.

The pneumatic response time of the sidestream infrared gas analyzer illustrated in FIG. 2 is limited by the speed with which a gas wavefront traverses the aperture 38 through the detection volume. A small optical aperture permits faster response times but decreases signal strength. In a preferred embodiment of the invention, aperture 38 is approximately 0.100" by 0.100" so that the pneumatic volume can pass through the detection volume quickly, thereby minimizing the pneumatic response time. Since discontinuities in the gas passageway adversely affect laminar flow, the gas passages 40 of the sample cell 10 are shaped to create smooth transitions from the generally round cross-sections of the gas inlet and outlet (for example, 0.60" diameter cross-section) to a 0.100" diameter cross-section and then to create smooth transitions to the 0.100" by 0.100" rectangular cross-section at aperture 38. The smooth transitions help maintain smooth, laminar flow of the respiratory gases through the sample cell 10 without turbulence or eddies which could distort the wavefronts.

The operation of the infrared source 14 and infrared detector 22 in the sidestream configuration of the invention are essentially the same as described in the aforementioned Yeldeman patents. The electronics and calibration of the sidestream gas analyzer of the invention may also be essentially the same as that described therein and, accordingly, such description is herein incorporated by reference. In addition, the processing technique of the invention may also incorporate the gas concentration computation techniques described by Yelderman et al. In U.S. patent application Ser. No. 07/782,991, also assigned to the same Assignee as the present invention and also herein incorporated by reference.

The present invention thus demonstrates the feasibility of constructing a sidestream infrared gas analyzer using an optically stabilized infrared detector of the type described in the Yelderman et al. patents. However, the present invention further incorporates an "optical funnel" to reduce the optical aperture from the infrared source and infrared detector in order to minimize the gas volume required for the pneumatic sample cell. Moreover, because of the streamlined geometry of the present invention, the optical path length and hence the response time of the device may be significantly reduced.

The present invention is ideally used in conjunction with a rebreathing apparatus to measure carbon dioxide ($CO_2$) and nitrous oxide ($N_2O$) levels in the expired air of a patient. As shown in FIG. 3, the present invention can provide a step response within 125 msec for a flow rate of 100 cc/minute. As also shown in FIG. 3, the response time is inversely proportional to the flow rate.

The performance of the sidestream infrared gas analyzer in accordance with the invention has been found to be at least as good as that of a mainstream infrared gas analyzer using similar components. However, the shorter path length and reflective walls of the sample cell 10 in the sidestream infrared gas analyzer of the invention allow an approximately 30% larger signal than that of a typical mainstream configuration. This increase in signal helps offset the reduction in modulation. The result is a signal to noise ratio substantially the same as that of a similar mainstream configuration. Of course, one skilled in the art may increase the optical path length in the sample cell of the invention, as desired, for use in measuring lower concentrations of gases of interest in other medical and industrial applications.

Although the present invention has been described with reference to a preferred embodiment, it will be understood by those skilled in the art that the invention is not limited to the embodiment specifically disclosed herein. Rather, those skilled in the art will appreciate that many variations of the specific embodiments described herein are intended to be within the scope of the invention as defined by the following claims.

We claim:

1. An infrared gas analyzer for detecting the concentration of a gaseous component of a substantially gaseous flow stream provided via an airway, comprising:

a source of infrared radiation having a first aperture;

an infrared energy detector disposed in an optical path of said infrared radiation so as to receive incident radiation from said infrared radiation source and to produce electrical signals representative of the received incident radiation, said infrared energy detector having a second aperture;

a sample cell disposed in a plane substantially perpendicular to said optical path said sample cell directing at least a portion of said substantially gaseous flow stream, in a direction substantially perpendicular to said optical path, between said infrared radiation source and said detector via a detection volume in said optical path, said sample cell comprising a gas passage for said substantially gaseous flow stream said sample cell having a cross-section which smoothly changes from a cross-section of said airway to a first aperture of said detection volume in a plane substantially parallel to said optical path so as to prevent turbulence in said substantially gaseous flow stream as it passes through said gas passage and said detection volume;

a first optical funnel in said optical path between said infrared radiation source and said detection volume which reduces a cross-section of said first aperture of said infrared radiation source to a cross section of a second aperture of said detection volume in a plane substantially perpendicular to said optical path without a measurable reduction in signal strength of said infrared radiation from said infrared radiation source as it passes through said first optical funnel and said detection volume;

a second optical funnel in said optical path between said detection volume and said infrared energy detector which increases a cross-section of said second aperture of said detection volume to a cross-section of said second aperture of said infrared energy detector without a measurable reduction in signal strength of said infrared radiation from said infrared radiation source as it passes through said second optical funnel and said second aperture of said infrared energy detector for detection by said infrared radiation detector; and processing means for processing said electrical signals representative of the received incident radiation so as to produce an indication of the concentration of said gaseous component in said substantially gaseous flow stream.

2. An analyzer as in claim 1, further comprising housing means for housing said infrared radiation source, said infrared energy detector, said sample cell and said first and second optical funnels, said infrared radiation source and said infrared energy detector being housed opposite each other in said housing so that they have aligned optical axes.

3. An analyzer as in claim 2, wherein said sample cell is removable from said housing means for cleaning and said sample cell further includes optical windows on opposite sides thereof in said optical path, said sample cell being calibrated to account for differential absorption effects of said optical windows so that respective sample cells are interchangeable.

4. An analyzer as in claim 3, wherein said optical windows comprise one of anti-reflective coated silicon and anti-reflective sapphire.

5. An analyzer as in claim 1, wherein said first and second apertures of said infrared radiation source and said infrared energy detector, respectively, and said first and second detection apertures of said detection volume have rectangular cross-sections and a cross-sectional area of said second detection aperture of said detection volume is less than half of a cross-sectional area of said first aperture of said infrared radiation source.

6. An analyzer as in claim 1, wherein said first and second optical funnels are treated by a material which is highly reflective of said infrared radiation.

7. An analyzer as in claim 6, wherein said highly reflective material comprises gold over a plating of nickel.

* * * * *